United States Patent [19]

Logan et al.

[11] Patent Number: 5,026,724
[45] Date of Patent: Jun. 25, 1991

[54] COMPOUNDS WITH BRONCHODILATOR ACTIVITY

[75] Inventors: Robert T. Logan, Lanark; James Redpath, Bishopbriggs; George McGarry, Airdrie; Robert G. Roy, Larkhall, all of Scotland

[73] Assignee: Akzo N.V., Arnhem, Netherlands

[21] Appl. No.: 375,654

[22] Filed: Jul. 5, 1989

[30] Foreign Application Priority Data

Jul. 5, 1988 [EP] European Pat. Off. ........ 88.306121.0

[51] Int. Cl.$^5$ .................... C07C 69/94; C07D 209/08
[52] U.S. Cl. ................................. 514/443; 514/826; 549/49; 549/51; 549/58
[58] Field of Search ..................... 549/49, 51, 58; 514/443, 826

[56] References Cited

U.S. PATENT DOCUMENTS

| | | | |
|---|---|---|---|
| 3,910,955 | 10/1975 | Chapman et al. | 549/49 |
| 4,158,015 | 6/1979 | Paul | 564/264 |
| 4,665,206 | 5/1987 | Redpath et al. | 549/51 |
| 4,705,782 | 11/1987 | Logan et al. | 514/150 |
| 4,737,519 | 4/1988 | Yamashita | 514/826 X |

*Primary Examiner*—Frederick E. Waddell
*Assistant Examiner*—Catherine Scalzo
*Attorney, Agent, or Firm*—William M. Blackstone

[57] ABSTRACT

A method is provided for treating patients suffering from or susceptible to bronchoconstriction, particularly for patients suffering from an asthmatic attach which comprises the use of benzothiophene, benzofuran, dihydronaphthalene or indene derivatives represented by formula I

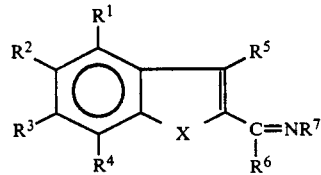

wherein each of $R^1$, $R^2$, $R^3$ and $R^4$ is independently H, (1-4C) alkyl, (1-4C) halogen substituted alkyl, OH, (1-4C) alkoxy, (1-4C) halogen substituted alkoxy, $NO_2$, CN, halogen, an unsubstituted or (1-4C) alkyl substituted amino group, or wherein two adjacent groups $R^1$, $R^2$, $R^3$ or $R^4$ together form methylenedioxy;
X is S, O or $(CH_2)_m$ in which m is 1 or 2;
$R^5$ is H or (1-4C) alkyl;
$R^6$ is H, $NH_2$ or (1-4C) alkyl;
$R^7$ is H, (1-4C) alkyl or $OR^8$ in which
$R^8$ is H, (1-4C) alkyl or (1-8C) acyl;
and its pharmaceutically acceptable salts for the preparation of a medicament with bronchodilator activity.

16 Claims, No Drawings

COMPOUNDS WITH BRONCHODILATOR ACTIVITY

The invention relates to the use of benzothiophene, benzofuran, dihydronaphthalene and indene derivatives for the preparation of medicaments with bronchodilator activity.

Currently, there exists no really suitable drugs that can be considered as drugs of choice for the treatment of asthma. This is despite attempts to improve bronchodilator efficacy of theophylline, which up to now is considered to be the most effective bronchodilator for the treatment of asthma. Unfortunately, however, this class of drugs is notorious for its low potency, poor bio-availability and very narrow therapeutic index. It would be therefore desirable to discover selective inhibitors of cyclic AMP phosphodiesterase or drugs with a different bronchodilator mode of action, which possess a beneficial bronchodilator effect but lack most of the adverse effects of theophylline.

Several benzothiophene derivatives are known in the art, for example compounds that possess positive inotropic effects for treating heart failure (e.g. British Patent Application 84.06906 and U.S. Pat. No. 4,705,782).

According to the invention there is provided a method for treating patients suffering from or susceptible to bronchoconstriction, particularly for patients suffering from an asthmatic attack which comprises the use of benzothiophene, benzofuran, dihydronaphthalene or indene derivatives represented by formula I

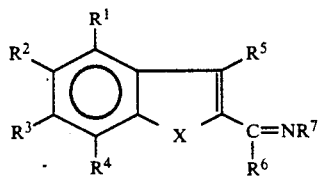

wherein each of $R^1$, $R^2$, $R^3$ and $R^4$ is independently H, (1-4C) alkyl, (1-4C) halogen substituted alkyl, OH, (1-4C) alkoxy, (1-4C) halogen substituted alkoxy, $NO_2$, CN, halogen, an unsubstituted or (1-4C) alkyl substituted amino group, or wherein two adjacent groups $R^1$, $R^2$, $R^3$ or $R^4$ together form methylenedioxy; is S, O or $(CH_2)m$ in which m is 1 or 2;

$R^5$ is H or (1-4C) alkyl;

$R^6$ is H or (1-4C) alkyl;

$R^7$ is H, (1-4C) alkyl or $OR^8$ in which $R^8$ is H, (1-4C) alkyl or (1-8C) acyl; and its pharmaceutically acceptable salts for the preparation of a medicament with bronchodilator activity Preferred compounds according to the invention have formula I wherein at least two of the groups $R^1$, $R^2$, $R^3$ and $R^4$ are independently OH, (1-4C) alkoxy or form together a methylenedioxy group, whereas the one or two remaining groups are independently H, $NO_2$, amino, (1-4C) alkyl substituted amino or halogen, of which F, Cl and Br are preferred, and wherein furthermore $R^5$ is H or $CH_3$, $R^6$ is H, $NH_2$ or $CH_3$ and $R^7$ is OH.

The most preferred compounds according to the invention have formula I wherein at least two of the groups $R^1$, $R^2$, $R^3$ and $R^4$ are independently OH, $OCH_3$ or $OC_2H_5$, whereas the one or two remaining groups are independently H, $NO_2$, F or Cl. In this most preferred embodiment X is S, O or $(CH_2)_2$, $R^5$ is H, $R^6$ is H or $NH_2$ and $R^7$ is OH. Of these most preferred compounds, the compounds wherein $R^2$ and $R^3$ are $OCH_3$, $R^1$ and $R^4$ are H, F or Cl, and especially H, X is S, O or $(CH_2)_2$, $R^5$ is H, $R^6$ is $NH_2$ and $R^7$ is OH, show the most pronounced bronchodilator activity.

The invention includes the use of pharmaceutically acceptable acid addition salts of the compounds of formula I, such as salts derived from inorganic acids, like sulphuric acid, hydrochloric acid, carbonic acid, and the like, or from organic acids like acetic acid, benzoic acid, citric acids, formic acid, fumaric acid, lactic acid, maleic acid, methanesulphonic acid, oxalic acid, tartaric acid, and the like. The preferred salts are derived from hydrochloric acid and methanesulphonic acid. The term (1-4C) alkyl used in the definitions of $R^1$ through $R^8$ includes groups like methyl, ethyl, propyl, isopropyl, butyl, isobutyl, sec-butyl and tert-butyl; the alkyl moiety of the (1-4C) alkoxy groups defined in $R^1$-$R^4$ has the same meaning as defined above. The term (1-8C) acyl used in the definition of $R^8$ includes groups derived from aliphatic and arylaliphatic carboxylic acids like acetic acid, propanoic acid, hexanoic acid, lactic acid, phenylacetic acid, benzoic acid and the like.

The medicaments according to this invention may be administered by various routes, including the oral, rectal, transdermal, subcutaneous, intravenous, intraperitoneal, intramuscular, inhalation, or intranasal routes.

The active ingredient according to formula I is preferably administered in a daily dose of 0.01 to 50 mg/kg body weight, and more preferably 0.2 to 20 mg/kg body weight.

The daily dose for humans of said active ingredient is about 0.05 to about 2000 mg, and preferably 10 to 500 mg. Deviations from the preferred dose regime are possible, dependent on the physical condition of the patient, the choice of route of administration and the experience and insight of the treating physician.

Preferred pharmaceutical forms of the present invention are capsules, tablets, suppositories, injectable solutions, creams and ointments. Especially preferred are formulations for inhalation or insufflation, such as an aerosol, and formulations for oral application.

Compounds of formula I show strong bronchodilator activity, which for instance can be measured by the relaxant effect of the compounds after tone contracture by histamine, which is determined as follows.

Isolated, single ring preparations of guinea-pig trachea were suspended in tissue baths containing KrebsHenseleit solution, at 37° C., bubbled with a gaseous mixture of 5% $CO_2$ and 95% $O_2$ Tissues were allowed to equilibrate for 60 min. after which flurbiprofen (1 $\mu M$), a cyclo-oxygenase inhibitor, was added to the tissue bath and a further 60 min. equilibration allowed to elapse. The flurbiprofen remained in contact with the tissue for the duration of the experiment in order to eliminate the complications that arise in guinea-pig airway preparations due to the spontaneous and agonist-induced generation of cyclo-oxygenase products (for example $PGE_2$ and $PGF_{2\alpha}$) No other drugs (e.g. atropine or $\beta$-adrenoceptor antagonists) were present during the experimental protocol.

In the presence of flubiprofen guinea-pig isolated airways do not develop any spontaneous tone. Thus, tone (contracture) was induced by addition of an equieffective ($EC_{50}$) concentration of histamine (40 $\mu M$). The relaxant effects of each compound were tested by constructing cumulative concentration-effect curves. In each experiment, three preparations were contracted with histamine. After completion of the relaxant concentration-effect curves the compound under test was thoroughly washed out from the preparations which were then left to recover to control levels of resting tension (approx. 60 min.).

Results of this test for the compounds of formula I are denoted in the table.

TABLE formula:

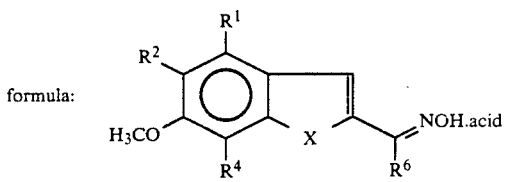

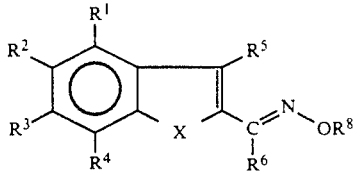

E

| $R^1$ | $R^2$ | $R^4$ | $R^6$ | X | acid | m.p. °C. | histamine-induced tone $EC_{50}$ [M] |
|---|---|---|---|---|---|---|---|
| H | OCH$_3$ | H | NH$_2$ | (CH$_2$)$_2$ | HCl | 203–205 | 3.0 × 10$^{-6}$ |
| Cl | OH | H | NH$_2$ | S | HCl | >190(dec) | 1.0 × 10$^{-5}$ |
| F | OCH$_3$ | H | NH$_2$ | S | CH$_3$SO$_3$H | 200–204(dec) | 2.5 × 10$^{-6}$ |
| H | OCH$_3$ | H | H(Z-isomer) | S | none | 211–215 | 5.0 × 10$^{-6}$ |
| H | OCH$_3$ | H | NH$_2$ | S | none | 215–217(dec) | 8.0 × 10$^{-6}$ |
| H | OCH$_3$ | H | NH$_2$ | S | HCl | 203–210 | 8.0 × 10$^{-6}$ |
| Br | OCH$_3$ | H | NH$_2$ | S | CH$_3$SO$_3$H | 196–202(dec) | 1.0 × 10$^{-6}$ |
| H | OCHF$_2$ | H | NH$_2$ | S | HCl | 178–182(dec) | 5.0 × 10$^{-6}$ |
| OCH$_3$ | H | H | NH$_2$ | O | HCl | 165–170 | 5.0 × 10$^{-6}$ |
| H | OCH$_3$ | H | H(E-isomer) | S | none | 205–213 | 2.0 × 10$^{-6}$ |
| H | OCH$_3$ | H | CH$_3$(E-isomer) | S | none | 224–229 | 1.0 × 10$^{-7}$ |
| Cl | OCH$_3$ | Cl | NH$_2$ | S | HCl | 172–196(dec) | 8.0 × 10$^{-6}$ |
| Cl | OCH$_3$ | H | H(Z/E mixture) | S | none | 183–189 | 5.0 × 10$^{-6}$ |

Many of the compounds employed in this invention are known in the art and can be prepared according to standard methods (see e.g. British Patent Application 84.069.06 and U.S. Pat. No. 4,705,782).

The Z- and E-isomers of the oximes of formula I are new compounds which can be prepared for instance from the Z/E mixtures of isomers (which are generally known, see e.g. J. Org. Chem., 26,359 (1961)) Methods of obtaining pure isomers, essentially free from the other isomer, include:

(a) Separation by crystallization.

(b) Separation by chromatography, preferably column chromatography using silica.

(c) Treatment of the Z/E mixture with an acid, preferably dry HCl in a suitable solvent, e.g. dioxan.

(d) Irradiation of the Z/E mixture in a suitable solvent, e.g. benzene.

The new compounds are represented by formula II

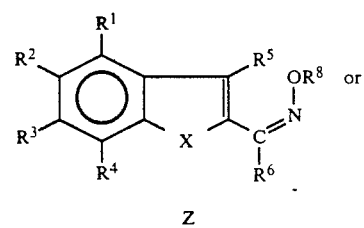

Z wherein each of R$^1$, R$^2$, R$^3$ and R$^4$ is independently H, (1-4C) alkyl, (1-4C) halogen substituted alkyl, OH, (1-4C) alkoxy, NO$_2$, CN, halogen, an unsubstituted or (1-4C) alkyl substituted amino group, or wherein two adjacent groups R$^1$, R$^2$, R$^3$ or R$^4$ together form methylenedioxy;

X is S, O or (CH$_2$)m in which m is 1 or 2;

R$^5$ is H or (1-4C) alkyl;

R$^6$ is H, or (1-4C) alkyl;

R$^8$ is H, (1-4C) alkyl or (1-8C) acyl with the proviso that if the compound has the E-configuration and R$^6$ is (2-4C) alkyl at least one of the groups R1- R$^5$ and R$^8$ is not H.

With the term (2-4C) alkyl is meant the same groups as mentioned hereinbefore in the definition of (1-4C) alkyl with the exclusion of the methyl group.

The oximes disclaimed in the above mentioned definition of compounds with the general formula II are known from EP 9865, which describes insecticidal compounds of said structures.

Compounds with the general formula I, wherein one or more of R$^1$, R$^2$, R$^3$ and R$^4$ represent (1-4C) halogen substituted alkoxy, R$^6$ is NH$_2$, and R5, R7, R8, and X have the meanings given before for compounds of general formula I, are also new.

Preferred compounds are those with one or more of R$^1$-R$^4$ is/are (1-4C) fluoro substituted alkoxy.

Methods of obtaining these new compounds are essentially the same as described in the hereinbefore mentioned British Application 84.06906.

These new compounds as such, their pharmaceutically acceptable salts and the pharmaceutical preparations containing these compounds also belong to the essential features of this invention.

The following examples further illustrate the preparation and formulation of the compounds used in this invention.

EXAMPLE 1

(Z)-5,6-dimethoxy-benzo[b]thiophene-2-carboxaldehyde oxime 19,75 g of a 1:1 mixture of (Z)- and (E)-5,6-dimethoxy-benzo[b]-thiophene-2-carboxaldehyde oxime was suspended in 197 ml of dry dioxan. Dry HCl gas was passed into the reaction mixture until a saturated solution was attained. After 1.5 h the product was isolated by addition of water (1 l) and filtration. Crystallization from CH$_2$Cl$_2$/MeOH gave pure Z-isomer (17,9 q). m.p. 211°–215° C.

EXAMPLE 2

(E)-1-(5,6-dimethoxy-benzo[b]thien-2-yl)-ethanone oxime and
(Z)-1-(5,6-dimethoxy-benzo[b]thien-2-yl)-ethanone oxime.

6,6 g of a 1:1 mixture of (Z)- and (E)-1-(5,6-dimethoxy-benzo[b]thien-2-yl)-ethanone oxime was chromatographed over silica. Elution with diethyl ether/dichloromethane mixtures gave the E-isomer (2.1 g). m.p. 224°–229° C.

The more polar Z-isomer was obtained on further elution (1.4 g) 225°–229° C.

EXAMPLE 3

In an analogous manner as n example 2 were prepared
(Z)-5,6-dimethoxy-benzo[b]thiophene-2-carboxaldehyde oxime. m.p. 210°–214° C.;
(E)-5,6-dimethoxy-benzo[b]thiophene-2-carboxaldehyde oxime. m p. 205°–213° C.;
(Z)-4-chloro-5,6-dimethoxy-benzo[b]thiophene-2-carboxaldehyde oxime. m.p. 194°–196° C.;
(E)-4-chloro-5,6-dimethoxy-benzo[b]thiophene-2-carboxaldehyde oxime. m.p. 183°–187° C.;
(Z)-6,7-dimethoxy-benzo[b]thiophene-2-carboxaldehyde oxime. m.p. 128°–129° C.;

EXAMPLE 4

In an analoqous manner as in example 2 were prepared:
(E)-6,7-dimethoxy-benzo[b]thiophene-2-carboxaldehyde oxime. m.p. 127°–128° C.;
(Z)-5,6-dimethoxy-benzo[b]furan-2-carboxaldehyde oxime. m.p. 197°–200° C.;
(E)-5,6-dimethoxy-benzo[b]furan-2-carboxaldehyde oxime; m.p. 150°–157° C.;
(Z)-1,2-dihydro-6,7-dimethoxy-naphthalene-3-carboxaldehyde oxime;
(E)-1,2-dihydro-6,7-dimethoxy-naphthalene-3-carbox-aldehyde oxime. m.p. 166°–169° C.;
(Z)-1-(5,6-dimethoxy-benzo[b]thien-2-yl)-propanone oxime;
(E)-1-(5,6-dimethoxy-benzo[b]thien-2-yl)-propanone oxime;
(E)-5,6-methoxy-benzo[b]thiophene-2-carboxaldehyde oxime. m.p. 178°–180° C.;
(Z)-5-methoxy-benzo[b]-thiophene-2-carboxaldehyde oxime. m.p. 202°–204° C.;
(E)-furano[2,3-f]-1,3-benzo-dioxole-6-carboxaldehyde oxime. m.p. 179°–181° C.;
(Z)-furano[2,3-f]-1,3-benzo-dioxole-6-carboxaldehyde oxime. m.p. 193°–195° C.;
(E)-5,6-dimethoxyindene-2-carboxaldehyde oxime m.p. 184°–187° C.
(Z)-5,6-dimethoxyindene-2-carboxaldehyde oxime. m.p. 181°–186° C.
(E)-4-fluoro-benzo[b]thiophene-2-carboxaldehyde oxime m.p. 190°–192° C.;
(Z)-4-fluoro-benzo[b]thiophene-2-carboxaldehyde oxime m.p. 182°–191° C.;

EXAMPLE 5

(a)
5-Difluoromethyloxy-6-methoxy-benzo[b]thiophene-2-carbonitrile

A mixture of 5-hydroxy-6-methoxy-benzo[b]thiophene-2-carbonitrile (10.30 g) and anhydrous potassium carbonate (7.63 g) was treated with a solution of dry dimethylformamide (110 ml) which has been previously saturated with chlorodifluoromethane gas. The mixture was then sealed in an autoclave, stirred, and heated to 40° C. After 3 days the reaction mixture was cooled and poured into water (700 ml). The resultant precipitate was iiltered off, dried, and extracted with hot dichloromethane (300 ml). The organic extract was concentrated then poured through a column of fine silica (200 g). The appropiate fractions were combined and evaporated to dryness to give 5-difluoromethyloxy-6-methoxy-benzo[b]thiophene-2-carbonitrile as an off-white solid (5.49 g), m.p. 99°–101° C.

(b)
5-Difluoromethyloxy-N-hydroxy-6-methoxybenzo[b]-thiophene-2-carboximidamide hydrochloride.

Sodium (1.46 g) was cut into small pieces and added to a stirred solution of methanol (50 ml) under an atmosphere of nitrogen. When all the sodium has dissolved the hot solution was treated with a warm solution of hydroxylamine hydrochloride (4.41 g) in methanol (50 ml) After 60 min. the white suspension of sodium chloride was filtered off and the filtrate was added to 5-difluoromethyloxy-6-methoxy-benzo[b]thiophene-2-carbonitrile (5.40 g). After 90 min. the resultant fine white suspension was poured into water (500 ml), stirred, and the white solid was filtered off and dried at 60° C. under vacuum to give 5-difluoromethyloxy-N-hydroxy-6-methoxy-benzo[b]thiophene-2-carboximidamide (5.76 g) m.p. 176°–177° C.

(c) Conversion to hydrochloride salt:

The free base (5.76 g) was suspended in methanol (120 ml) and the mixture was stirred and acidified to pH 1 using a solution of dry hydrogen chloride gas in methanol. The free base dissolved. The resultant solution was filtered dust-free, concentrated and then crystallized from methanol and diethyl ether to give 5-difluoromethyloxy-N-hydroxy-6-methoxy-benzo[b]thiophene-2-carboximidamide hydrochloride as a white solid (6.02 g), m.p. 167°–180° C. (dec.).

EXAMPLE 6

A tablet is prepared using the ingredients below.

| | |
|---|---:|
| N-hydroxy-5,6-dimethoxy-benzo[b]thiophene-2-carboximidamide hydrochloride | 50 mg |
| microcrystalline cellulose | 25 mg |
| dicalciumphosphate dihydrate | 72.2 mg |

| | |
|---|---|
| corn starch | 22.5 mg |
| hydroxypropyl cellulose (HPC) | 3.5 mg |
| magnesium stearate | 1.8 mg |

The active principle, microcrystalline cellulose, dicalciumphosphate dihydrate and corn starch are mixed. An aqueous HPC solution is added and the mass is granulated in several minutes. The resulting mass is dried, sieved and magnesium stearate is added. After mixing the mass is compressed to form tablets each weighing 175 mg.

EXAMPLE 7

In an analogous manner tablets were prepared containing as active ingredient:

4-bromo-N-hydroxy-5,6-dimethoxy-benzo[b]thiophene-2-carboximidamide methanesulphonate;

1,2-dihydro-N-hydroxy-6,7-dimethoxy-naphthalene-3-carboximidamide;

4-chloro-N-hydroxy-5,6-dimethoxy-7-methylaminobenzo-[b]thiophene-2-carboximidamimide hydrochloride;

5,6-dimethoxy-benzo[b]thiophene-2-carboxaldehyde oxime;

(Z)-5,6-dimethoxy-benzo[b]thiophene-2-carboxaldehyde oxime;

(E)-5,6-dimethoxy-benzo[b]thiophene-2-carboxaldehyde oxime;

1-(5,6-dimethoxy-benzo[b]thien-2-yl-) ethanone oxime;

4-chloro-5,6-dimethoxy-benzo[b]thiophene-2-carboxaldehyde oxime;

6,7-dimethoxy-benzo[b]thiophene-2-carboxaldehyde oxime;

4-chloro-N-hydroxy-5,6-dimethoxy-benzo[b]thiophene-2carboximidamide hydrochloride;

5-difluoromethyloxy-N-hydroxy-6-methoxy-benzo[b]thiophene-2-carboximidamide hydrochloride;

N-hydroxy-4,6-dimethoxy-benzo[b]furan-2-carboximidamide;

4-cyano-N-hydroxy-5,6-dimethoxy-benzo[b]thiophene-2carboximidamide hydrochloride;

N-hydroxy-5,6-dimethoxy-3-methyl-benzo[b]thiophene-2carboximidamide hydrochloride;

5,6-dimethoxy-benzo[b]thiophene-2-carboximidamide hydrochloride;

5,6-dimethoxy-N-methyl-benzo[b]thiophene-2carboximidamide hydrochloride;

5,6,N-trimethoxy-benzo[b]thiophene-2-carboximidamide hydrochloride.

EXAMPLE 8

An aerosol solution is prepared containing the following component:

| | weight % |
|---|---|
| N-hydroxy-5,6-dimethoxy-benzo[b]furan-2-carboximidamide hydrochloride | 0.25 |
| ethanol | 25.00 |
| Propellant 11 (trichlorofluoromethane) | 10.75 |
| Propellant 12 (dichlorodifluoromethane) | 29.50 |
| Propellant 114 (dichlorotetrafluoroethane) | 29.50 |

The active compound is dissolved in ethanol and the solution is added to the propellant 11, cooled to −30° C. and transferred to a filling device. The required amount is then fed to a container and further filled with the pre-mixed propellants 12 and 114 by means of the cold-filled method or pressure-filled method. The valve units are then fitted to the container. Examole 9

In an analogous manner aerosol solutions were prepared containing as active ingredient:

N-hydroxy-4,6-dimethoxy-benzo[b]thiophene-2-carboximidamide hydrochloride;

N-hydroxy-5,6-dimethoxy-4-nitro-benzo[b]thiophene-2-carboximidamide methanesulphonate;

4-fluoro-N-hydroxy-5,6-dimethoxy-benzo[b]thiophene-2-carboximidamide;

4,7-dichloro-N-hydroxy-5,6-dimethoxy-benzo[b]thiophene-2-carboximidamide hydrochloride;

N-hydroxy-5,6-dimethoxy-benzo[b]thiophene-2-carboximidamide;

4-chloro-5,N-dihydroxy-6-methoxy-benzo[b]thiophene-2-carboximidamide hydrochloride;

5,6-methylenedioxy-N-hydroxy-benzo[b]thiophene-2-carboximidamide hydrochloride;

5,6-methylenedioxy-benzo[b]thiophene-2-carboxaldehyde oxime;

(Z)-5,6-methylenedioxy-benzo[b]furan-2-carboxaldehyde oxime;

(E)-6,7-methylenedioxy-1,2-dihydro-naphthalene-3-carboxaldehyde oxime.

We claim:

1. Method of treating asthma in a patient, comprising adminstering a bronchodilating effective amount of a compound of the formula I

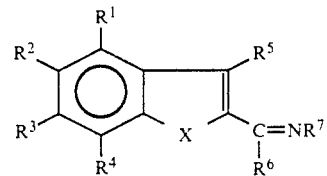

wherein each of $R^1$, $R^2$, $R^3$ and $R^4$ is independently H, (1-4C) alkyl, (1-4C) halogen substituted alkyl, OH, (1-4C) alkoxy, (1-4C) halogen substituted alkoxy or halogen, X is S;

$R^5$ is H or (1-4C) alkyl;

$R^6$ is H, $NH_2$ or (1-4C) alkyl; and $R^7$ is H, or (1-4C) alkyl or $OR^8$ in which $R^8$ is H, (1-4C) alkyl or (1-8C) acyl; or its pharmaceutically acceptable salts.

2. Method according to claim 1 wherein at least two of the groups selected from $R^1$, $R^2$, $R^3$ and $R^4$ are independently OH or (1-4C) alkoxy and the one or two remaining groups are independently H or halogen, $R^5$ is H or $CH_3$, $R^6$ is H, $NH_2$ or $CH_3$ and $R^7$ is OH or their pharmaceutically acceptable salts.

3. Method according to claim 1 wherein at least two of the groups selected from $R^1$, $R^2$, $R^3$ and $R^4$ are independently OH, $OCH_3$ or $OC_2H_5$, and the one or two remaining groups are independently H, F or Cl, and X is S, $R^5$ is H, $R^6$ is H or $NH_2$ and $R^7$ is OH, or their pharamceutically acceptable salts.

4. Method according to claim 1 wherein $R^2$ and $R^3$ are $OCH_3$, $R^1$ and $R^4$ are H, F or Cl, X is S, $R^5$ is H, $R^6$ is NH₂ and R⁷ is OH or their pharmaceutically acceptable salts.

5. Method according to claim 4 wherein R¹ and R⁴ are hydrogen.

6. A compound having bronchodilating activity of the formula

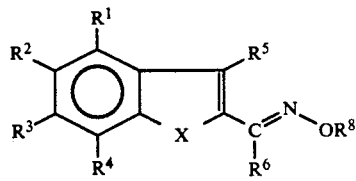

wherein the oxime group consists of the geometrical E-isomer, essentially free from its Z-isomer, in which R¹, R², R³ and R⁴ are independently H, (1-4C) alkyl, (1-4C) halogen substituted alkyl, OH, (1-4C) alkoxy, (1-4C) halogen substituted alkoxy or halogen and at least one of R¹, R², R³ and R⁴ is (1-4C)halogen substituted alkyl, OH, (1-4C) alkoxy, (1-4C) halogen substituted alkoxy or halogen, R⁵ is H or (1-4C)alkyl, R⁸ is H, (1-4C)alkyl or (1-8C) acyl and x is S, and R⁶ is H or (1-4C) alkyl, with the proviso that if R⁶ is (2-4C) alkyl at least one of the groups R¹–R⁵ and R⁸ is not H.

7. Compound according to claim 6, in which R¹, R⁴, R⁵ and R⁶ are H, R² and R³ are OCH₃, and X is S.

8. Compound of the formula I

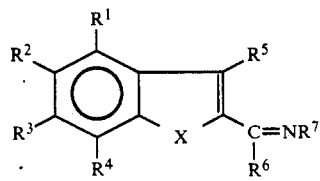

wherein one or more of R¹, R², R³ and R⁴ represent (1-4C) halogen substituted alkoxy, R⁶ is NH₂, R⁵ is H or (1-4C) alkyl, R⁷ is H or (1-4C) alkyl, or OR⁸ in which R⁸ is H, (1-4C) alkyl or (1-8C) acyl and X is S, and its pharmaceutically acceptable salts.

9. Pharmaceutical composition comprising a bronchodilating effective amount of a compound according to claim 8.

10. Pharmaceutical composition comprising a broncho-dilating effective amount of a compound according to claim 6 and a pharmaceutically acceptable carrier.

11. Pharmaceutical composition comprising a broncho-dilating effective amount of a compound according to claim 7 and a pharmaceutically acceptable carrier.

12. A compound having bronchodilating activity of the formula

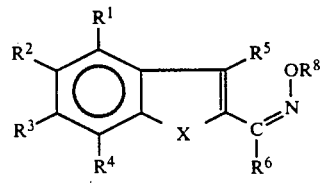

wherein the oxime group consists of the geometrical Z-isomer, essentially free from its E-isomer, in which R¹, R², R³, and R⁴ are independently H, (1-4C) alkyl, (1-4C) halogen substituted alkyl, OH, (1-4C) alkoxy, (1-4C) halogen substituted alkoxy or halogen and at least one of R¹, R², R³ and R⁴ is (1-4C) halogen substituted alkyl, OH, (1-4C) alkoxy, (1-4C) halogen substituted alkoxy or halogen, R⁵ is H or (1-4C) alkyl, R⁸ is H, (1-4C) alkyl or (1-8C) acyl, X is S, and R⁶ is H or (1-4C) alkyl with the proviso that when R⁶ is (2-4C) alkyl at least one of the groups R¹–R⁵ and R⁸ is not H.

13. Compound according to claim 12, in which R¹, R⁴, R⁵ and R⁶ are H, R² and R³ are OCH₃, and X is S.

14. A pharmaceutical composition comprising a bronchodilating effective amount of a compound according to claim 12 and a pharmaceutically acceptable carrier.

15. A compound according to claim 7, wherein R⁸ is H.

16. A compound according to claim 13, wherein R⁸ is H.

* * * * *